United States Patent
Hewitt et al.

(10) Patent No.: US 9,265,482 B2
(45) Date of Patent: Feb. 23, 2016

(54) ULTRASOUND TRANSDUCER CONNECTOR

(71) Applicants: Robert A. Hewitt, Sammamish, WA (US); Robert Patrick Hunt, Sammamish, WA (US); Robert Nolen Phelps, Sammamish, WA (US)

(72) Inventors: Robert A. Hewitt, Sammamish, WA (US); Robert Patrick Hunt, Sammamish, WA (US); Robert Nolen Phelps, Sammamish, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 235 days.

(21) Appl. No.: 13/945,791

(22) Filed: Jul. 18, 2013

(65) Prior Publication Data

US 2015/0025390 A1    Jan. 22, 2015

(51) Int. Cl.
*A61B 8/00* (2006.01)
(52) U.S. Cl.
CPC ............ *A61B 8/4411* (2013.01); *A61B 8/4444* (2013.01)

(58) Field of Classification Search
CPC ........................... A61B 8/4411; A61B 8/4483
USPC ..................... 600/459; 439/38, 219
See application file for complete search history.

(56) References Cited

U.S. PATENT DOCUMENTS

| 5,615,678 | A | 4/1997 | Kirkham et al. |
| 5,882,310 | A | 3/1999 | Marian, Jr. |
| 6,887,204 | B2 * | 5/2005 | Nozaki et al. ................ 600/459 |
| 8,033,174 | B2 | 10/2011 | Shin et al. |
| 2008/0243003 | A1 * | 10/2008 | Crunkilton et al. ........... 600/459 |
| 2010/0062633 | A1 * | 3/2010 | Puttinger et al. ............. 439/352 |
| 2012/0143062 | A1 | 6/2012 | Nordgren et al. |

* cited by examiner

*Primary Examiner* — Joel Lamprecht

(57) ABSTRACT

A reversible transducer connector allows the connector to be inserted within the receptacle in more than one orientation. The electrical connections between the receptacle and connector are reprogrammed based on the orientation. The connector is inserted in two or more stages, such as using zero-insertion or magnetic retention in a first stage to identify the connector and using an automated engagement to engage remaining channel connections in a second stage for use. Doors for protecting the connector and/or receptacle may be opened and/or closed magnetically.

24 Claims, 2 Drawing Sheets

ULTRASOUND TRANSDUCER CONNECTOR

BACKGROUND

The present invention relates to transducer connectors. In particular, a transducer is releasably connected to a system.

In medical diagnostic ultrasound, an imaging system has one or more receptacles. Detachable ultrasound probe assemblies are connected to the receptacles. For the probe assembly, a transducer array is housed in a hand-held probe. The hand-held probe is connected through a cable to a connector. The connector electrically and mechanically releasably connects to the ultrasound system. The user can select different ultrasound probes for different examinations and connect the selected probe to the ultrasound imaging system. Using beamformers and other circuitry in the ultrasound imaging system, an image is generated through the transmission and reception of acoustic energy by the connected transducer probe.

To place the connector into one of the receptacles, the user forces the connector into the receptacle. The connector must be aligned in a specific manner with the receptacle, which may result in the cable extending in an undesired or inconvenient direction and may be difficult to align given the positioning of the receptacle on the imaging system.

The force, a mechanical latch, or automatic latch holds the connector in place in the receptacle for use. When disconnecting the transducer assembly, the user releases the latch and/or applies sufficient force to remove the connector from the receptacle. It may be difficult for the user to apply the force in the required direction. Any latching may be difficult given the user's position relative to the receptacle.

BRIEF SUMMARY

By way of introduction, the preferred embodiments described below include methods and systems for a transducer connector system. A reversible connector allows the connector to be inserted within the receptacle in more than one orientation. The electrical connections between the receptacle and connector are reprogrammed based on the orientation. The connector is inserted in two or more stages, such as using zero-insertion or magnetic retention in a first stage to identify the connector and using an automated engagement to engage remaining channel connections for use in a second stage. Doors for protecting the connector and/or receptacle may be opened and/or closed magnetically. Any of the reversible, multi-stage, magnetic door, or zero-insertion may be used alone. Any combination of two or more of these techniques may be used.

In a first aspect, a transducer connector system is provided for ultrasound. A transducer assembly includes a transducer and a connector. An ultrasound device includes a receptacle. The connector is matable with the receptacle in first and second orientations and in first and second stages of retention. Each stage of retention has a different retention force. The receptacle is configured for detection of a presence of the mating and the first or second orientation when the connector mates with the receptacle in the first stage. The first stage avoids channel contacts. The channel contacts are formed in the second stage.

In a second aspect, a transducer connector system is provided for ultrasound. A receptacle is operable to receive the connector reversibly. A beamformer has channels connectable with a transducer when the connector is received by the receptacle.

In a third aspect, a method is provided for connecting a transducer with a system. A first housing is mated with a second housing to a first extent. The first and second housings are drawn together to a second extent greater than the first extent after the mating. An identification of the transducer is detected when the first and second housings are mated at the first extent. The transducer is operated when the first and second housings are drawn to the second extent.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

A reversible, two-stage interconnect, magnetic door latching, and/or zero-insertion-force ultrasound connector and connector scheme is provided. For example, a pinless connector may be inserted through multiple stages, reversibly, and with zero-insertion force into a pinned receptacle. In one embodiment, the receptacle doors are opened and closed magnetically. Upon insertion, the connector is maintained in the receptacle in a first stage by one or more magnets. While inserted in the first stage, engagement pins are used to detect the presence of the connector, type of the transducer, and orientation of the connector installed within the receptacle and without making a final or full connection of all contacts. The type of the transducer is read by the ultrasound system from a PROM in the connector. In the second stage, a selected transducer makes the final or full connection of the contacts needed for scanning with the transducer.

The reversible interconnect allows the user to orient the transducer to allow the dressing of the cable to either the right, left or other angle along the system. The magnetic retention of the ultrasound probe jack in the receptacle provides for zero-insertion force. The multiple stage insertion allows for use of guide pins or contacts designed to make first contact when the probe connector is initially installed to detect the presence, type, and orientation of transducer and a final connection with the probe contacts only for when the transducer is to be used. Electro-mechanical drawing of the connector into the receptacle in the second stage avoids manual manipulation by the user other than to select the transducer for use in the system's user interface.

Example embodiments use a medical diagnostic ultrasound imaging system. A phased array of transducer elements is to be releasably connected with the system, so a multi-channel connector is used. In other embodiments, the connection system is used for therapeutic ultrasound. In yet other embodiments, these concepts may be extended to other fields besides medical ultrasound. This connector system may be used in any application where an error free interconnect of a group of electrical contacts is used.

Figure 1:
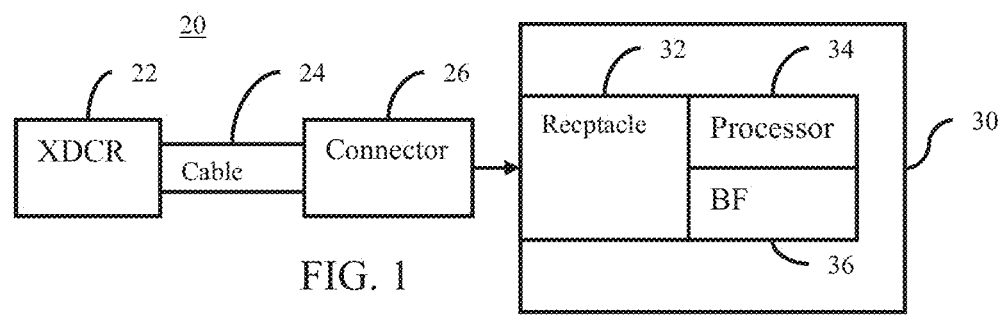
FIG. 1 is a block diagram of a transducer connector system in one embodiment.

FIG. 1 shows one embodiment of a transducer connector system for ultrasound. The transducer connector system includes a transducer assembly 20 and an ultrasound device 30. The transducer assembly 20 is shown disconnected from the ultrasound device 30. The detachable transducer assembly 20 allows selection of different transducers with different frequency responses or other characteristics for imaging by the ultrasound device 30. By connecting the transducer assembly 20 to the ultrasound device 30, the ultrasound device 30 uses the transducer assembly 20 to scan a patient.

The ultrasound transducer assembly 20 includes a transducer 22 in a handheld probe housing 22, a cable 24, and a connector 26. The cable 24 connects the probe housing 22 to the connector 26. Additional, different or fewer components may be provided. For example, a hand-held system is provided where the transducer probe housing 22 is included as part of the connector 26 without the cable 24. The transducer assembly 20 provides a detachable transducer for connecting and disconnecting from the ultrasound system 30. As another example, beamforming or other signal processing circuitry is provided in the probe housing 22 and/or the connector 26.

The transducer probe housing 22 is plastic, metal, rubber, combinations thereof or any other now-known or later-developed material for housing the transducer 22, such as an array of transducer elements. In one embodiment, the transducer probe housing 22 is shaped for hand-held use, such as being sized and shaped for holding with a hand and having a grip. In other embodiments, the transducer probe housing 22 is shaped for use internal to a patient, such as shaped as an endoscope or catheter. The transducer probe housing 22 at least partially houses an array of elements, such as covering a portion of the array and allowing a face of the array acoustical access for scanning a patient.

The array of elements is an array of piezoelectric, multilayer piezoelectric, capacitive membrane ultrasound transducer or other now-known or later-developed elements for converting between electrical and acoustical energies. One or multidimensional arrays are provided with full or sparse sampling. For example, a two-dimensional array has M elements (e.g., 1,920 or other number) fully-sampled in a square or rectangular grid positioned on a planar or curved surface. As another example, a one dimensional array has 64, 128, 192, or 256 fully sampled elements. The transducer array includes a flex circuit, signal traces or other structures for electrical interconnection from the elements of the array to other electronics or wires of the probe assembly 20. For example, the flex circuits are connected to a plurality of coaxial cables in the cable 24.

The cable 24 includes a plurality of coaxial cables connected with the ultrasound transducer 22. For example, 64, 128, 192 or other number of coaxial cables are provided for transmitting electrical signals representing acoustic energy received at elements of the array or to be used to generate acoustic energy. Each coaxial cable receives information for one element or information representing a plurality of different elements. In alternative embodiments, the cable 24 is a flexible circuit, optical data path, fiber optic, insulated wires or other now-known or later-developed structure. For example, analog-to-digital converters are provided in the transducer probe housing 22, and digital signals are transmitted along now-known or later-developed digital paths through the cable 24. The cable 24 electrically connects the ultrasound transducer 22 to the connector 26. Where multiplexing or partial beamforming is provided, fewer cables than elements may be used.

Figure 3:
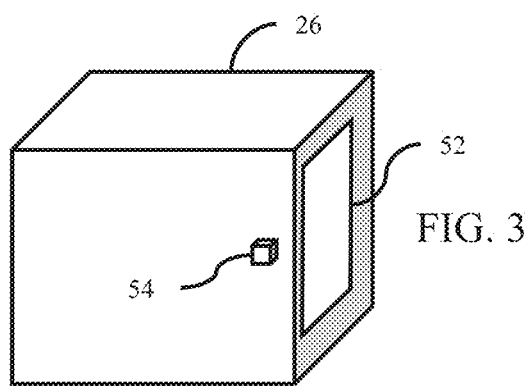
FIG. 3 illustrates one embodiment of a connector.

The connector 26 is metal, plastic, rubber, combinations thereof or other now-known or later-developed material for housing or at least partially enclosing an array of contacts 52 (see FIG. 3). In one embodiment, the connector 26 is metal to provide radio frequency shielding at least partially coated with rubber or plastic to provide a grip.

Figure 2:
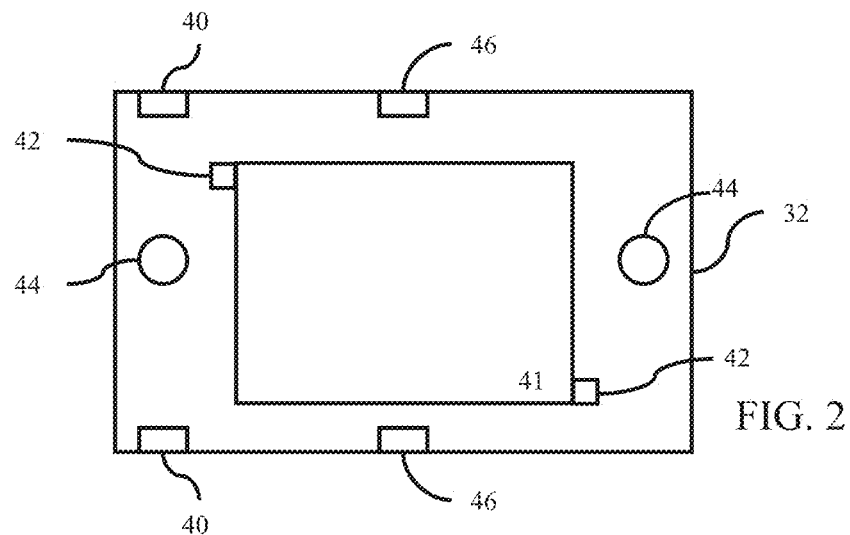
FIG. 2 illustrates one embodiment of a receptacle.

Additional, different or fewer components may be included within the connector 26. For example, termination resistors or passive tuning circuits connect with each of the cables for providing an impedance match. As another example, a memory for transducer identification, guide pins 42, sensors 40, magnets 44, and/or latches 46 of FIG. 2 are included.

The connector 26 is connected at the end of the cable 24, so that the connector 26 is spaced from the ultrasound transducer array 32 and associated probe housing 22. In other embodiments, the cable 24 is not provided and the transducer housing 22 and connector 26 are formed in a unitary housing.

The connector 26 is shaped to allow detachment and attachment to the receptacle 32 of the ultrasound system 30. In one embodiment, now-known connector housings are used, such as a generally cuboid box. Any size or shape may be provided.

The connector 26 houses contacts 52 for electrical connection with the receptacle. The contacts 52 provide transducer or beamformer channel, ground, power, control, and/or memory or identification connections. Any number of contacts 52 may be provided. The contacts 52 are pads, prongs, wires, traces, guide posts, contact surfaces, pins, or other device for making detachable electrical contact. In one embodiment, the mating surface of the connector 26 is a printed circuit board that has a matching pattern of metal pads for electrical contact with pins of the receptacle 32. 192 or other number of electrical connections of exposed metallic traces or pads on a circuit board are recessed within the connector 26 for mating with pins. Metal fingers on the interior of the receptacle 32 are used to make contact between the receptacle 32 and the connector 26. In other embodiments, the contacts 52 are the metal fingers for making contact with pads in the receptacle 32.

Combinations of pads and prongs may be used for the contacts 52. In one embodiment, an outer surface of the connector 26 or a pad or series of pads are used as a grounding contact surface. When in contact with the receptacle 32, the contact surface connects ground between the connector 26 and the receptacle 32. Pads of the contacts 52 provide for channel connections. Metalized guide posts 42 provide connections for control signals, power, and/or identification. Other combinations of electrical connectors may be used.

FIG. 1 shows one connector 26 and corresponding transducer assembly 20 for releasable connection with the receptacle 32 of the ultrasound system 30. More than one transducer assembly 20 may be connected. For example, the user selects one of several transducer assemblies 20 and inserts the corresponding connector 26 into the receptacle. The ultrasound system 30 may have more than one receptacle, such as having two or three receptacles. A corresponding number or fewer number of transducer assemblies 20 may be connected to respective receptacles 32.

The ultrasound system 30 is a medical diagnostic ultrasound imaging system. Additionally or alternatively, the ultrasound system 30 is a therapeutic ultrasound system. Ultrasound is transmitted into the patient using the transducer 22. The ultrasound system 30 generates electrical waveforms for the transmission. The electrical waveforms are provided to the receptacle 32 for transmission to the transducer 22, where the electrical energy is transduced into acoustic energy. Similarly, the transducer 22 may receive acoustic echoes and convert the echoes into electrical signals. The received signals are provided through the connector 26 and the receptacle 32 to the ultrasound system 30. The ultrasound system 30 processes the received electrical signals to generate an image. In other embodiments, the ultrasound system 30 is a computer, work station or other medical imaging system.

The ultrasound system 30 includes a transmit beamformer and a receive beamformer, shown collectively as a beamformer 36. The transmit beamformer is operable to generate waveforms for transmitting acoustic energy along one or more beams at the same time. The receive beamformer is operable to receive electrical signals from acoustic echoes and form samples representing spatial locations in the patient.

The electrical signals generated by the transmit beamformer are routed to the receptacle 32 and then to the connector 26. The receptacle 32 also electrically connects the connector 26 to the receive beamformer. The connections within the ultrasound system 30 from the receptacle 32 are made through one or more switches, such as a transmit and receive switch. The beamformer 36 is configured to provide a wideband interface, such as a switching matrix with 128, 192 or 384-wire impedance controlled paths from the receptacle 32 to the beamforming cards or slots on the printed circuit board interconnects. Other switching matrix and number of paths may be provided. When the connector 26 is seated within the receptacle 32, the electrical signals may pass along various channels between the transducer 22 and the beamformer 36.

The transmit beamformer includes pulsers, waveform generators, memories, phase shifters, delays, amplifiers, or other components for generating a transmit waveform. The components are provided for different channels so that relatively delayed and apodized transmit waveforms are generated. Digital and/or analog transmit beamformers may be used.

The receive beamformer is an analog or digital receive beamformer. The receive beamformer is configured to receive analog signals at a radio frequency band (e.g., a band centered at 2-10 MHz), but may be configured to receive either analog or digital signals at the same or different frequency bands. In one embodiment, the receive beamformer includes separate beamformers for different imaging modes, such as a separate spectral Doppler beamformer and a B-mode and color-flow mode beamformer. For example, the receive beamformer is a processor on a printed circuit board, ASIC or other device. The receive beamformer includes a plurality of delays, amplifiers and one or more summers. The electrical signals representing different elements or groups of elements are relatively delayed, apodized, and then summed to form samples or signals representing different spatial locations along one or more receive beams.

Further processes and associated circuitry are implemented by the ultrasound system 30 for generating an image, applying therapeutic ultrasound, or for calculating measurements from the receive beamformed information. For example, a B-mode detector, Doppler estimator, spectral Doppler processor, scan converter, temporal filter, and/or spatial filter are provided. Different, additional or fewer transmit and receive circuit devices or components may be provided.

The transmit beamformer, receive beamformer and receptacle 32 are at least partially enclosed within a system housing. The system housing is plastic, metal, wood, fiberglass, or any other now-known or later-developed material for housing electronics. In one embodiment, the system housing is a workstation or cart-based housing supported on wheels or resting on the floor. In other embodiments, the system housing is a lap top or other portable-sized device, such as a suitcase-sized portable ultrasound system. In yet another embodiment, the system housing is a hand-held ultrasound system, such as a PDA or scope-shaped housing.

The receptacle 32 is one of any now-known or later-developed mechanical and electrical connectors for detachably connecting and removing the transducer assembly 20. The receptacle 32 includes grooves, extensions, latches, screws, threaded holes or any other now-known or later-developed mechanical structure for releasably connecting to another device. A plurality of male or female electrical connections for connecting with individual digital traces, such as in a circuit board configuration, or for connecting with coaxial cables is provided. For example, compliant (e.g., spring) metal prongs or pins are arranged in an array. One or more contact pads may alternatively or additionally be used. The mating between the receptacle contacts and the connector contacts 52 is to be by metal to metal compression, but other mating may be provided.

The receptacle 32 is installed in the system 30 and is permanently attached. Contact attachment between the system 30 and the receptacle 32 is provided through press fit, through-hole, or solderless attachment methods (e.g., metal to metal compression, conductive epoxy, conductive polymer, etc.). Additional mechanical support for the receptacle may be provided by mechanical hardware to prevent stress on the electrical contacts. Less permanent but more permanent than the connection with the connector 26 may be provided.

Referring to FIGS. 1 and 2, the receptacle 32 may include one or more sensors 40. The sensors 40 detect the presence of the connector 26. For example, an optical sensor is provided. An optical emitter and detector are arranged so that either the absence or presence of light indicates either the absence or presence of the connector 26. For example, when the connector 26 is inserted sufficiently into the receptacle 32, a light beam is blocked or activated. Rather than using a sensor relying on light transmission, the absence of ambient light may be used. Alternative sensors include contact or mechanical sensors, such as a pressure switch. Electrical sensors may be used. The existence or absence of an electrical contact may be used. The connector 26 positioned in or against the receptacle 32 completes or interrupts a circuit, which indicates that the connector 26 is installed or removed. An electrical contact also used for other purposes may operate as the sensor 40. Only one or more than one sensor 40 may be used.

The sensor 40 detects the presence or not of mating. Where multiple stages of contact are provided, the sensor 40 detects only one stage, detects all the stages as the same, or detects the specific stage of the mating. The same or different sensors detect the different stages. Alternatively, mating without stage specific detection is sensed.

Referring to FIG. 1, the processor 34 is a sensor, detector, circuit, general processor, digital signal processor, field programmable gate array, control processor, digital circuit, analog circuit, or combinations thereof. The processor 34 interacts with the receptacle 32 for communicating with the ultrasound system 30, such as communicating information to be used in the user interface, and/or for controlling the mating.

The processor 34 is configured by hardware and/or software to detect an identification of the transducer 22 in the transducer assembly 20. The identification is specific to the assembly 20 or generalized to the type of transducer 22. For example, when the receptacle 32 receives the connector 26, the processor 34 queries a memory in and/or receives data from the connector 26. The data indicates characteristics of the transducer 22, such as the type and/or frequency of operation.

The processor 34 is configured to detect the orientation, stage of insertion, and/or other information. Using one or more electrical connections established between the connector 26 and the receptacle 32, the processor 34 outputs data used to determine a response by the system 30 to mating, or the processor 34 determines the response of the system 30 to mating.

In one embodiment, the connector 26 is reversible relative to the receptacle 32. The receptacle 32 may receive the connector 26 in two or more orientations. The connector 26 is reversible in the sense of connection 180 degrees apart or opposite or is reversible in the sense of two or more orientations at any number of degrees difference. The connector 26 may mate with the receptacle 32 in different orientations. For example, the connector 26 and receptacle 32 have rectangular or oblong shapes. The connector 26 fits within or around the receptacle 32 with the same shape, at least for the mating surfaces. As rectangular or oblong, only two different orientations are possible. Using square, triangular, star, circular or other shapes without preventative measures or devices, more than two orientations are possible. The same connector 26 fits against the receptacle while providing electrical connections in two or more different orientations.

Polarization of the connector 26 is removed to allow the user to insert the connector 26 into the receptacle 32 in different orientations. This frees the user from needing to be concerned with the orientation between the receptacle 32 and connector 26, speeding mating of the connector 26. If the cable 24 mounts with the connector 26 at an angle, such as coming off of one side or in a given direction other than orthogonal to the receptacle 32, there may be an advantage to a given orientation. For example, sonographers for radiology tend to have the cable 24 to the left of the system 30 while sonographers for cardiology tend to have the cable 24 to the right of the system 30. By allowing the sonographer to select an orientation, the cable 24 may be more easily managed.

Since the ultrasound system 30 relies on specific electrical connections, the orientation is detected for arranging the electrical connections. As shown in FIG. 2, one or more guide pins 42 are used to indicate the orientation. The guide pins 42 are prongs, posts, slots, or other mechanical structure for guiding the connector 32 relative to the receptacle. By having diagonal positions in the rectangular arrangement, the reversible connection is allowed. To detect the orientation, one or more guide pins 42 include electrical contacts or pads. The electrical connection indicates the orientation. For example, one guide pin 42 has electrical connections and the other does not. By sensing the electrical contact, the orientation is determined.

As another example, one guide pin 42 provides a ground connection and the other a signal connection. By detecting which of the guide pins 42 is grounded relative to the connector 26, the orientation is determined by the processor 34. In one embodiment, two guide pins 42 in the receptacle 32 provide electrical contact to the connector 26 and a 1-Wire PROM. One contact is used for data/power and another wire is used for ground. The two guide pins 42 of the receptacle 32 are connected to the processor 34 in the system 30, such as a field programmable gate array (FPGA). The FPGA determines the presence and orientation of the probe connector 26 by which of the two wires or guide pins 42 is grounded. The FPGA then configures itself to use the other wire or guide pin 42 for data/power and to read the identification information from the 1-wire PROM.

In other embodiments, the orientation is detected by the presence sensor 40. For example, the presence may be detected by one sensor 40 and not another, such as where one is blocked for one orientation and not for another orientation. Other contacts than guide posts may be used, such as attempting to read identification information from two or more electrical contacts. The electrical connection receiving the response or identification information indicates the orientation.

Once the orientation is determined, the electrical connections are arranged to account for the orientation. The connector 26 and/or the receptacle 32 have programmable electrical connections. For example, an FPGA in the receptacle 32 is reconfigured depending on the orientation. The reconfiguring assigns different functions, channels, or other operation to different electrical contacts. A switch matrix is configured to assign channel contacts based on the orientation. For example, the contacts 41 (e.g., compliant pins) of the receptacle 32 include channel connections to the beamformer 36. The channels are assigned to particular elements of the transducer 22. In one orientation, the contacts 41 have one assignment (e.g., contact 1 to element 128) but a different assignment (e.g., contact 1 to element 1) in another orientation. One or more electrical connections may be the same regardless of orientation or all contact assignments change.

Contacts 41, 52 for other functions, such as ground, power, signaling, and/or identification are assigned based on orientation. Alternatively, one or more contacts are the same regardless of orientation. For example, by placement in the center and/or duplicative placement in a diagonal, the same contacts may be used regardless of orientation.

Reversibility is handled through the use of redundant contacts, symmetrical placement of common contacts, and/or programmability in the system 30 or the connector 26 to reassign functionality to contacts. The pinout of the connector 26 is to be chosen and programmability of system functions and interconnectivity allow the removal of polarization.

In an additional or alternative embodiment, the connector 26 is insertable into the receptacle 32 in stages. Different amounts of insertion are provided for different purposes, different connections, and/or different amounts of retention force. The stages represent discontinuous insertion rather than a continual sliding. Latches, switches, blocks, springs, amounts of insertion force, differences in insertion mechanisms, or other differentiators result in different stages of insertion.

In one embodiment, different forms of retention and/or different amounts of retention force distinguish between the two stages. By using different forms or amounts of force, two or more stages of insertion are provided. Differences in electrical connections for the stages may alternatively or additionally be provided.

A first stage is associated with the user inserting the connector 26. The connector 26 is maintained in the receptacle 32 by friction or the user. A counteracting force may be provided, such as one or more springs applying a force to push the connector 26 out or at least require further force to further insert. In one embodiment, the connector 26 is maintained at the first stage by a retention magnet 44. The retention force is provided by any friction and magnetic energy. The magnetic energy is from a permanent magnet or a coil (e.g., electro magnet) activated with electrical energy to provide magnetic force. One or more magnets 44 are positioned to hold the connector 26 in the receptacle 32. In the first stage, the connector 26 is held in place by the use of permanent magnets or electro-magnets.

The magnets 44 may assist in insertion. Rather than forcing the user to overcome all the friction or apply all the insertion force, the magnets 44 attract magnets or magnetic material in the connector 26. A zero-insertion-force connection is provided. Zero-insertion force may require some insertion force, but require less than would otherwise exist. The magnetic energy assists in insertion. In other embodiments, the magnetic energy on the connector 26 adjacent to but not in the receptacle 32 is greater than or equal to the force needed to insert the connector 26, so the user merely places the connector 26 at the desired orientation and the magnets 44 pull the connector into the receptacle in the first stage. The zero-insertion force, whether true zero force by the user or with user assistance, allows the user to place the connector 26 into the receptacle 32 for the first stage.

For the second stage, a different mechanism and/or amount of force is applied to further insert and/or to retain the connector 26 in the receptacle 32. For example, an electro-mechanical latch 46 (see FIGS. 2 and 4) is activated. The electromechanical latch 46 includes a motor to move the latch in response to electrical energy and a shaped device or structure to apply force from the motor to the connector 26 and/or receptacle 32. For example, a motor rotates an arm to pull or press the connector 26 into the receptacle 32. The arm operates on a prong 54 or other structure of the connector 26. The arm may be shaped such that further rotation applies more force. Other latching mechanisms may be used, such as a slidable ramp structure. In other embodiments, additional magnetic force is applied, such as applying a greater current in an electro-magnet.

The greater retention force overcomes resistance maintaining the connector 26 at the first stage. For example, a counteracting spring force is overcome. As another example, a tighter fit or greater friction is overcome. In other embodiments, the second stage has greater retention force, but a same position as the first stage. In either case, the retention force or force to remove the connector 26 from the receptacle 32 is greater in the second stage than the first stage. In other embodiments, a blocking device is moved to allow movement into the second stage so that a same retention force is applied to both stages, but with a difference in blocking.

The increase of retention force or transition to stage two is applied automatically or without user application of insertion force. Insertion by electro-mechanical or other non-user device frees the user of having to manipulate some type of mechanical lever to accomplish the task of mating the connector 26. Elimination of the manual latching mechanism in the connector 26 may allow for more of the full volume of the interior of the connector housing to be available for use for additional components. Retention of the connector 26 through electro-mechanical or other device may also prevent the user from inadvertently removing the connector 26 from the receptacle 32 during operation without requesting removal from the system 30. Requesting removal of the connector 26 from the system 30 allows the system 30 to prepare and eject the connector 26 without disruption to system operation.

In one embodiment, each of the different stages corresponds to a different number of electrical connections between the connector 26 and the receptacle 32. When the connector 26 mates with the receptacle 32 in the first stage, beamformer channel and/or element connections are avoided. Channel contacts are avoided. The first stage is used for presence detection, transducer identification, and/or orientation determination. For example, the guide pins 42, metal fingers or prongs longer than others, contacts in different positions or raised, and/or other contacts are used to determine the type of transducer and orientation. Information used to reprogram or establish the channel contacts 41 and/or 52 is detected in the first stage. Specific contacts 41, 52 in the connector 26 and receptacle 32 are designed to make contact during the first stage of insertion in order to detect the presence, type and orientation of the connector. The first stage allows connection to a set of pins that communicate the presence of the connector, its orientation, and any ID information to verify the type of connector inserted.

In the second stage, the channel contacts are formed. Based on the increased force, electrical activation, and/or change in position between the first and second stages, the connector 26 is fully seated or seated sufficiently to allow use of the transducer 22 by the beamformer 36. Alternatively, the pins 41 are raised or moved to establish the electrical contacts of the second stage without further seating change between the connector 26 and the receptacle 32. The second stage mates the contacts of the receptacle 32 with the pinless pads of the connector 26.

Since a motor causes the connector 26 to seat, the motor may be used to control wiping. The placement of the contacts together may wipe built-up material, increasing electrical conductivity. The amount of wipe may depend on the angle of the contacts to the pads, the amount of force, and/or other factors in mating. To increase the amount of wipe or more likely decrease build-up materials, the motor may be controlled to cause a variation in the force, seating, or wiping profile. For example, the motor is reversed one or more time in rapid succession (e.g., within milliseconds) to use the wipe to scrub or repetitively wipe. As another example, intermittent change in speed during a wipe may aid in removal of build up. Alternatively, the motor causes the seating and corresponding wipe with a steady or regular force.

The different stages may be used for different purposes. Rather than fully seat the connector 26, the connector 26 is maintained in the first stage when not being used but remains connected to the system 30. The second stage is for use of the transducer 22 for scanning. In another approach, the first stage is provided for user placement and the second stage is provided for automated completion of the insertion. Where automated entry into the second stage is provided, the second stage is entered after sensing that a connector 26 has been installed in the receptacle 32 by the user.

For removal, the user may manually apply sufficient force to overcome the retention force. Where a latch is used, the user may activate reversal of the latch. For example, the user selects a different transducer to be used. The system 30 automatically releases the latch. Any ejection mechanism may be provided. In the case of a power failure, the system detects the loss of AC power and unlatches all the connectors 26 or the user manually releases the connector 26 from the receptacle 32.

The processor 34 may control transition from the first to second stage. Where only one connector 26 is in a single receptacle 32, the processor 34 may automatically draw the connector 26 into the second stage. Delay associated with determining the presence and type of transducer may be provided before automatically connecting. Alternatively, the processor 34 does not cause transition until a triggering event, such as a user configuring the system 30 of a particular application appropriate for the type of transducer 22.

Where there are multiple connectors 26 in respective receptacles 32, all of the connectors 26 may be initially in stage one. Alternatively, one connector 26 may be at stage two and the rest at stage one. The processor 34 selects a transducer to use, such as in response to a user input of a selection and/or in response to configuration of the system 30 for imaging appropriate for a specific transducer 22. If another transducer 22 is at stage two and no longer going to be used, that respective connector 26 is transitioned to stage one and the transducer 22 appropriate for the next scanning is transitioned to stage two. The processor 34 selects one transducer 22 and places the various transducers 23 at the appropriate stages. For example, the electro-mechanical latches 46 are activated to release and/or latch in response to the selection, thus increasing the retention force and providing electrical connections for scanning with one transducer and reducing or maintaining the retention force for other transducers associated with no electrical connections for scanning.

Once the system 30 detects that there is a new connector 26 installed (i.e., at stage one), the system 30 either auto-connects the connector 26 as in a single connector system or, in a multi-connector system, waits for a prompt from the user to connect the connector 26. In a multi-connector system where multiple identical connectors 26 are to be selected individually, only one connector is mated (e.g., stage two) to the system 30 at a time, allowing elimination of relays for selecting receptacles. This may reduce system cost and complexity. In one embodiment, multiple receptacles 32 are provided, but relays for switchably connecting different receptacles 32 to the beamformer 36 are not provided. In other embodiments, relays are provided.

Figure 4:
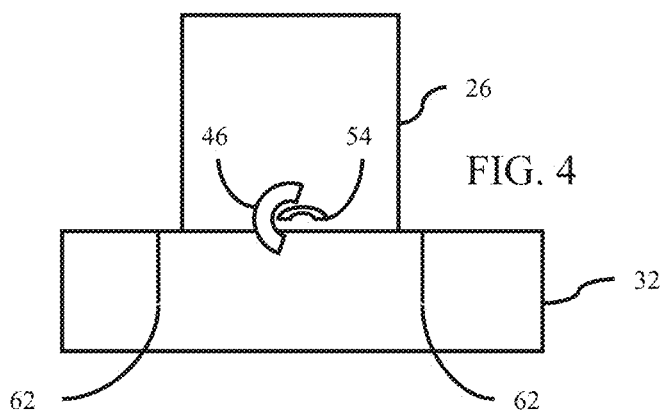
FIG. 4 illustrates one embodiment of an electro-mechanical latch.

The connector 26 and/or the receptacle 32 may include one or more doors 62 (see FIG. 4). The doors 62 protect the contacts 41, 52 when not in use and protect the user from exposure to current from the contacts 41, 52. The doors 62 are closed when the connector 26 is not inserted, but open for or during insertion. The doors 62 may be spring loaded such that inserting the connector 26 opens the doors 62 and withdrawing the connector 26 closes the doors 62.

In one embodiment, the doors 62 open in response to magnetic force. Permanent or electro-magnets in the doors 62 and the connector 26 provide the force to open the doors 62 with little or no contact. In other embodiments, a magnetic latching is used. Magnets hold the doors closed. When a magnet on the connector 26 is in proximity, the magnets holding the doors closed are slid apart or overpowered to open the doors 62. Other magnetic arrangements may be used.

Figure 5:
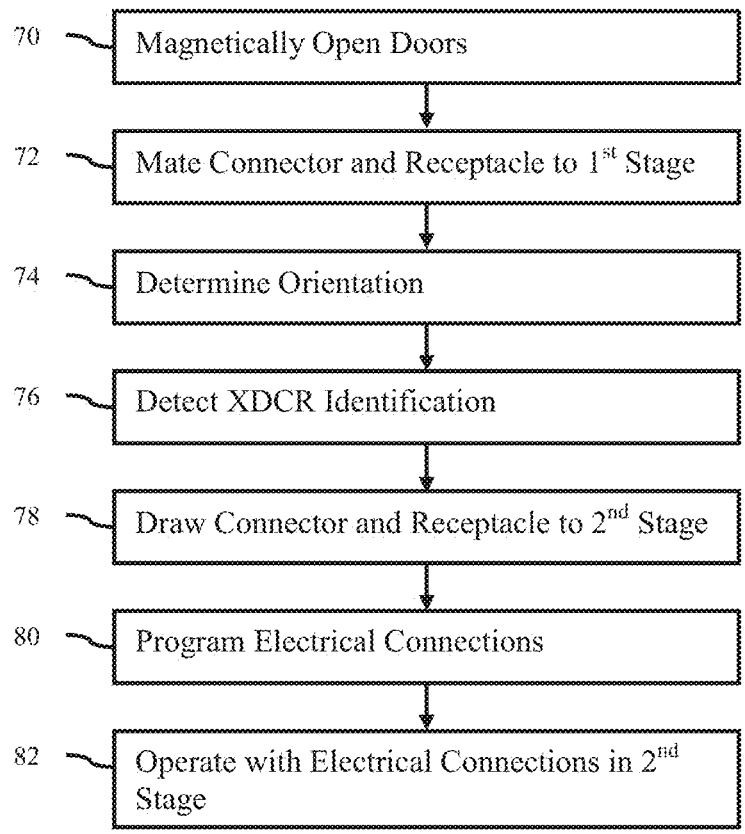
FIG. 5 is a flowchart diagram of one embodiment of a method for connecting a transducer with a system.

FIG. 5 shows one embodiment of a method for connecting a transducer with a system. The connecting is reversible, occurs in different stages, has magnetic door opening, and/or uses magnetic retention. Different, additional or fewer acts may be provided. For example, only the acts associated with the desired features are performed.

The method of FIG. 5 is implemented using the systems, connectors, receptacles, or other devices discussed above with respect to FIGS. 1 through 4 or other systems, connectors, receptacles, or devices. The method is performed in the order shown or a different order. For example, acts 74 and 76 are reversed in order. As another example, acts 78 and 80 are reversed in order.

In act 70, doors are magnetically opened. The doors on the connector and/or the receptacle are opened. The connector is on the transducer assembly or the system and is opposite the receptacle.

The doors are opened by magnetic force. The doors are pushed open or unsealed by applying the magnetic force. Bringing a magnet into proximity to the doors repels one or more magnets in the door. Alternatively, magnetic attraction is used to shift a magnet holding the door closed to another position so that the force holding the doors closed is removed or weakened. Springs, gravity, or other force may operate against the magnetic force.

The doors are opened to allow the mating of the connector with the receptacle. In response to the doors opening, the connector may be inserted into the receptacle.

In act 72, the connector is mated with the receptacle. One housing is positioned in or around another housing. Other interlocking structures may be used, such as both housing including male and female arrangements that align.

The housings are mated by complete insertion or by insertion to a limited extent. For example, the housings are mated to a first stage. The housings are pushed together, but not completely or fully seated. A spring, friction, or mechanism may limit the insertion. Alternatively, full or limited insertion is provided but with a limited retention force for mating to the first extent.

In one embodiment, a magnet assists the mating. The magnet or magnets attract the housings together, providing for zero-insertion force. The pulling together by magnetic energy may be limited, such as by the magnitude of the magnetic force used, a counteracting force, or a stop. The magnetic energy may additionally or alternatively be used to maintain a retention force, such as maintaining the housings in a first stage.

In act 74, the orientation of one housing relative to another housing is determined. Where the connection is reversible, one housing may be mated with the other in more than one orientation. The orientation is determined. The placement of a ground connection, signal connection, mechanical switch, interfering structure, or other orientation distinguishing feature is determined. Electrical, optical, or mechanical devices sense the orientation. In one embodiment, the position of a ground or signal contact in one of two possible locations is detected. The isolation of the ground or signal contact indicates the orientation.

In act 76, the identity of the transducer is detected. The partially or fully mated transducer is polled for identification information. For example, data is transmitted or pulled from a memory of the transducer by the system. The data indicates the type of transducer, a transducer serial number, and/or transducer operation characteristics. In another approach, a code is received and a look-up table in the system determines the identity from the code. The settings appropriate for the transducer are provided by the memory or look-up based on data from the memory.

In act 78, the housings are drawn together to a greater extent. The drawing together may be a physical drawing. The mating is increased, such as one housing being further inserted into the other. The mating may be increased by moving the pads or pins or other structure of the electrical connections into contact or into greater contact. The drawing to a greater extent may be by increased retention force instead or in addition to further physical engagement (i.e., further insertion). It may be made more difficult to remove one housing from the other or otherwise disconnect the electrical connections. In a multi-connector system, there may be another probe active on the system. The other probe may have a different connection requirement, so the re-organization of the contacts in act 80 does not take place until the previous connector has been ejected and the new selection has been connected.

In act 80, electrical contacts are programmed as a function of the relative positioning. The orientation indicates which electrical contacts connect with which elements of the transducer. The electrical contacts are programmed to route the signals to and from the elements to the desired beamformer channels for application of appropriate delays, phasing, and/or apodization. The programming allows for different orientations to be used. The physical pin layout is the same, but the use of the pins is reprogrammed as appropriate for the orientation.

All, some, or none of the electrical contacts may be programmed. For example, the orientation of one housing relative to another is the same as for the previous usage. The electrical contacts are maintained. As another example, one electrical contact may be at a center, so is mated with the same contacts regardless of orientation. Multiple electrical contacts may be used for the same channel, power, signal, or ground. By positioning such electrical contacts along a diagonal to the mating surface, duplicate electrical contacts may be maintained regardless of orientation.

The housings are drawn together to a greater extent by electrical, mechanical, and/or magnetic energy. For example, a motor moves a latch, pin, or other structure to add retention force or move the housings or contacts relative to each other. As another example, a current applied to an electro-magnet is increased.

In act 82, the transducer is operated. When the housings are mated for operation, such as drawn together to the greater extent, the transducer may be used by the system. Electrical signals to or from the transducer pass through the electrical connections.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A transducer connector system for ultrasound, the system comprising:
    a transducer assembly comprising a transducer and a first connector; and
    an ultrasound device comprising a first receptacle, the first connector matable with the first receptacle in first and second orientations and in first and second stages of retention, each stage of retention having a different retention force;
    wherein the first receptacle is configured for detection of presence of the mating and the first or second orientation when the first connector mates with the first receptacle in the first stage, the first stage avoiding channel contacts of beamformer channels in the first receptacle with the first connector, the channel contacts of the beamformer channels in the first receptacle being formed with the first connector in the second stage.

2. The system of claim 1 wherein the ultrasound device is a medical diagnostic ultrasound imaging system and wherein the transducer assembly comprises the transducer in a hand-held probe housing connected by a cable to the first connector.

3. The system of claim 1 wherein the first connector and the first receptacle are rectangular or oblong such that the first connector is matable with the first receptacle only in the first and second orientations.

4. The system of claim 1 wherein the first receptacle further comprises a switch matrix configured to assign the channel contacts based on the detection of the first or second orientation.

5. The system of claim 1 wherein the first stage of retention has a retention force based on magnetic retention such that less force is used to insert the first connector into the first receptacle.

6. The system of claim 1 wherein the first receptacle further comprises at least one guide pin operable to electrically connect with the first connector in the first stage, the electrical connection indicating the first or second orientation.

7. The system of claim 1 further comprising a processor configured to read an identification of a type of the transducer in the first stage of retention.

8. The system of claim 1 further comprising an electro-mechanical latch configured to increase a retention force from the first stage to the second stage.

9. The system of claim 8 wherein the ultrasound device comprises a second receptacle, the first connector in the first receptacle at the first stage, and a second connector in the second receptacle in the first stage;
    further comprising a processor configured to select the transducer for the first connector, the electro-mechanical latch responding to the selection by increasing the retention force and forming the channel contacts between the first connector and the first receptacle, the second connector maintained in the first stage relative to the second receptacle while the first connector and the first receptacle are in the second stage.

10. The system of claim 9 wherein the ultrasound device is free of relays for selecting between the first receptacle and second receptacle.

11. The system of claim 8 wherein the electro-mechanical latch is configured to vary a wiping during the increase in the retention force from the first stage to the second stage.

12. The system of claim 1 wherein the first receptacle further comprises at least one door, the door configured to open in response to magnetic force from a magnet.

13. The system of claim 1 wherein the first receptacle further comprises an optical sensor, the optical sensor positioned to detect the presence of the first connector in the receptacle.

14. A transducer connector system for ultrasound, the system comprising:
    a connector;
    a receptacle operable to receive the connector reversibly;
    a transducer connected with the connector and having a plurality of transducer elements; and
    a beamformer having channels in the receptacle and connectable with the transducer when the connector is received by the receptacle, the connector or receptacle being programmable to geometrically redefine element locations in connections of the channels to the transducer elements.

15. The system of claim 14 wherein the receptacle is operable to receive the connector in at least two different orientations of the connector relative to the receptacle, the connector or the receptacle having programmable electrical connections assigned functions based on the orientation of the connector to the receptacle.

16. The system of claim 14 further comprising a magnet positioned to hold the connector in the receptacle.

17. The system of claim 14 further comprising contacts on the connector and a processor, the processor configured to detect an orientation and an identification of the transducer from the contacts when the receptacle receives the connector.

18. The system of claim 14 wherein the receptacle is configured to receive the connector in different stages, each of the different stages corresponding to a different number of electrical connections between the connector and the receptacle.

19. The system of claim 14 further comprising a door operable to open magnetically for the receptacle to receive the connector.

20. A method for connecting a transducer with a system, the method comprising:

mating a first housing with a second housing to a first extent;

drawing the first and second housings together to a second extent greater than the first extent after the mating;

detecting an identification of the transducer when the first and second housings are mated at the first extent; and operating the transducer when the first and second housings are drawn to the second extent.

21. The method of claim 20 wherein mating comprises mating the first and second housing reversibly;

further comprising determining a relative position of the first housing to the second housing and programming electrical contacts for beamformer channels in the first housing as a function of the relative position.

22. The method of claim 20 wherein mating comprises magnetically pulling the first and second housing together and limiting the pulling to the first extent.

23. The method of claim 20 further comprising magnetically opening doors protecting the first housing, the opening allowing the mating.

24. The method of claim 20 wherein drawing comprises overcoming a resistance to moving the first and second housing from the first extent to the second extent, wherein detecting comprises detecting by a processor, and wherein operating comprises scanning by an ultrasound system using the transducer.

* * * * *